United States Patent [19]

Boyer et al.

[11] Patent Number: 5,385,837
[45] Date of Patent: Jan. 31, 1995

[54] ALKALINE PROTEASES DERIVED FROM *BACILLUS PROTEOLYTICUS*

[75] Inventors: Ernest W. Boyer, Elkhart, Ind.; Graham S. Byng, Woodinville, Wash.

[73] Assignee: Solvay Enzymes, Inc., Houston, Tex.

[21] Appl. No.: 181,872

[22] Filed: Jan. 13, 1994

Related U.S. Application Data

[63] Continuation of Ser. No. 884,184, May 18, 1992, abandoned.

[51] Int. Cl.$^6$ .......................... C12N 9/54; C12N 9/52; C12N 9/56; C11D 7/42
[52] U.S. Cl. .................................. 435/221; 435/270; 435/222; 252/174.12; 252/DIG. 12
[58] Field of Search ....................... 435/220, 221, 222; 252/174.12, DIG. 12

[56] References Cited

U.S. PATENT DOCUMENTS

| | | | |
|---|---|---|---|
| 3,622,458 | 11/1971 | Murao et al. | 435/222 |
| 3,674,643 | 7/1972 | Aunstrup et al. | 435/221 |
| 3,723,250 | 3/1973 | Aunstrup et al. | 435/221 |
| 3,827,938 | 8/1974 | Anustrup et al. | 435/221 |
| 4,002,572 | 1/1977 | te Nijenhuis | 252/99 |
| 4,052,262 | 10/1977 | Horikoshi et al. | 435/221 |
| 4,480,037 | 10/1984 | Ichishima et al. | 435/221 |

FOREIGN PATENT DOCUMENTS

| | | |
|---|---|---|
| 0204342 | 12/1986 | European Pat. Off. . |
| 0328229 | 8/1989 | European Pat. Off. . |
| 0405901 | 1/1991 | European Pat. Off. . |
| 0405902 | 1/1991 | European Pat. Off. . |
| 0415296 | 3/1991 | European Pat. Off. . |
| 0496361 | 7/1992 | European Pat. Off. . |
| 0510673 | 10/1992 | European Pat. Off. . |
| 2140064 | 1/1973 | France . |
| 8806624 | 9/1988 | WIPO . |
| 9100279 | 3/1991 | WIPO . |
| WO91/06637 | 5/1991 | WIPO . |
| WO91/02792 | 3/1992 | WIPO . |

OTHER PUBLICATIONS

Bender et al. (1966) *J. Am. Chem. Soc.*, 88, 5890–5913.
Biotechnology Abstracts, Derwent Publications Ltd., London GB. Abstract No. 85-09765, N. W. Koltukova et al., 1985, vol. 21, No. 3 pp. 361–364 (Prikl. Biokhim. Mikrobiol, vol. 21, No. 3, pp. 361–364 (1985) (Abstract only).
Markland, F. S. & Smith, E. L., *The Enzymes*, 3d Ed., vol. 3, (1971), pp. 561–608.
E. L. Smith et al., Journal of Biology Chemistry, vol. 243, No. 9 (1968), p. 2184.
The Genus Bacillus, 1973, Agriculture Handbook No. 427 (1973), U.S. Department of Ariculture.
Bergey's Manual of Systematic Bacteriology, vol. 2, (1986).

*Primary Examiner*—Douglas W. Robinson
*Assistant Examiner*—Jon P. Weber
*Attorney, Agent, or Firm*—Willian Brinks Hofer Gilson & Lione

[57] ABSTRACT

Alkaline proteases derived from specific bacteria of the species *Bacillus proteolyticus* have enhanced stability and improved washing ability when blended in general detergents. Also disclosed are new bacteria producing these alkaline proteases. Additionally, there is also disclosed a process for the production of the alkaline proteases which comprises cultivating new bacteria and detergent compositions containing these alkaline proteases.

1 Claim, No Drawings

ALKALINE PROTEASES DERIVED FROM *BACILLUS PROTEOLYTICUS*

This is a continuation of application Ser. No. 07/884,184 filed May 18, 1992 now abandoned.

BACKGROUND OF THE INVENTION

1. Field of the Invention

The invention relates to novel alkaline proteases derived from a new species of the genus Bacillus and their derivatives. The invention relates also to a new bacterium producing this alkaline protease and also to derivatives of this bacterium. The invention concerns also a process for the production of this alkaline protease which comprises cultivating the new bacterium. The invention concerns the uses of this alkaline protease, a detergent composition containing said alkaline protease and a method for removing protein stains from cloth.

2. Discussion of Related Art

Bacterial proteases which have the ability of degrading proteins at pH levels above 9 and higher have been known for some time. These proteases are suitable for inclusion in detergent formulation due to their protein degrading function maintaining its activity at the relatively high pH levels typically employed in detergent cleaning operations.

Among the known high alkaline proteases are those disclosed by Takashi in published European Patent Application 0204342 which claims an alkaline protease produced by a microorganism belonging to the genus Bacillus which organism exhibits certain characteristics and the alkaline protease produced thereby.

In the article The Journal of Biological Chemistry, 1968, 243, n° 9, p. 2184 the complete amino acid sequence of Subtilisin Carlsberg is described.

U.S. Pat. No. 4,052,262 to Horikoshi et al. claims a process for preparing an alkaline protease which involves the cultivation of a bacterium identified as Bacillus sp. No. 221 (ATCC 21522) in a suitable nutrient growth medium.

Ichishima et al. claim an alkaline protease identified as API-21 and characterized by certain physicochemical properties in U.S. Pat. No. 4,480,037. This protease is obtained by the cultivation which the patentees characterize as Bacillus sp. N° NKS-21.

In U.S. Pat. No. 3,723,250 Aunstrup et al. disclose a method for preparing high alkaline proteases, particularly those having optimal proteolytic activity at a pH value above about 9 and which retain at least 80% of their maximum proteolytic value at pH 12, by cultivation of certain bacteria from the genus Bacillus.

In U.S. Pat. No. 4,002,572 Nijenhuis discloses Bacillus strain "PB 92" and claims the use of this strain in the production of an enzyme having high proteolytic activity in alkaline media.

Aunstrup et al. claim a method for the production of an alkaline proteolytic enzyme which involves the submerged cultivation of the microorganism designated as *B. firmus*, strain NRS 783 in U.S. Pat. No. 3,827,938.

U.S. Pat. No. 3,674,643 to Aunstrup et al. claims a method for preparing a proteolytic enzyme by cultivating *B. alcalophilus* Vedder in a suitable nutrient medium at a pH between 7.5 and 11.

SUMMARY OF THE INVENTION

The present invention relates to novel alkaline proteases which have enhanced stability and demonstrate improved washing ability when blended in general detergents. The invention provides enzymes which have excellent stability in highly alkaline conditions and in the presence of detergents. The invention provides enzymes which have a greater enzymatic activity above pH 8.5 than the known alkaline proteases, this difference is most dramatic under highly alkaline conditions.

The present invention relates to alkaline proteases derived from a bacterium of the species *Bacillus proteolyticus*.

The present invention relates to alkaline proteases derived from a Bacillus, having a molecular weight of 28 Kdaltons and an isoelectric point from 10 to 11.5.

The alkaline proteases according to the invention have an isoelectric point of about 11.1, where its activity is maximum.

The enzymes according to the invention are extracellular high alkaline proteases.

The alkaline proteases of the present invention have an optimal pH for proteolytic activity at a pH in the range of 8.5 through 11.5 and usually of 10 or higher.

The alkaline proteases of the present invention have an amino terminal sequence as follows:
Ala-Gln-Ser-Val-Pro-Trp-Gly-Ile-Ser-Arg-Val-Gln-Ala-Pro-Ala-Ala-His-Asn-Arg-Gly- The alkaline proteases of the present invention retain at least 70% of their original activity after being held at a pH of 8.0 at a temperature of 43° C. for a period of 11 days in a commercial heavy duty liquid detergent. The alkaline proteases retain at least 50% of their original activity after being held at pH 8.0 or pH 9.6 at 43° C. for a period of 11 days.

The alkaline proteases of the present invention are derived from a Bacillus. Preferably they are derived from an alkalophilic Bacillus. More preferably they are derived from a bacterium of the species *Bacillus proteolyticus* or their derivatives by natural modification or by genetic modification.

The present invention concerns also novel bacteria of the species *Bacillus proteolyticus*.

The present invention concerns also novel bacteria of the species *Bacillus proteolyticus* producing alkaline proteases according to the invention. Preferably it concerns bacteria of the species *Bacillus proteolyticus* deposited with the Agricultural Research Culture Collection (Peoria, Ill., USA) under the Budapest Treaty. The deposit numbers are as follows: *Bacillus proteolyticus* strain 11-12: NRRL B-18964, *Bacillus proteolyticus* strain 11-13: NRRL B-18963, *Bacillus proteolyticus* strain 21-23: NRRL B-18965. All of these deposits were made on Apr. 17, 1992, at the Agricultural Research Culture Collection located at 1815 N. University Street, Peoria, Ill., 61604, U.S.A.

The present invention concerns also natural or artificial mutants and derivatives of the bacteria of the species *Bacillus proteolyticus*.

DETAILED DESCRIPTION OF PREFERRED EMBODIMENTS

The bacteria of the present invention belong to a new species of the genus Bacillus and secrete a protease having excellent stability in highly alkaline conditions, which protease, in the presence of detergent constituents, contribute to improved washing activity.

The microbiological properties of bacteria which we have characterized as *Bacillus proteolyticus* are determined according to R. E. Gordon, W. C. Haynes and C. H. N. Pang (1973)(The genus Bacillus. Handbook N°

427. U.S. dept of Agriculture, Washington, D.C.) and Bergey's Manual of Systematic Bacteriology Vol. 2 (1986). Media of pH 9.7 are prepared by adding 0.9% dibasic sodium phosphate and 1.0% sodium bicarbonate (pH adjusted with sodium hydroxide).

The following morphological properties are observed after culturing at 34° C. for 2 days on an agar medium comprised of 0.5% TRYPTONE (Difco), 0.5% yeast extract (Difco), 1.0% glucose and the buffering salts mentioned above. Thus, it is determined that all the cells of the strains comprising the new species Bacillus proteolyticus have the shape of rods. Strain 21–23 has a size of about 0.94 μm/2.35 μm. In addition, all of the strains have peritrichous flagella, showing motility and all of them formed spores which are ellipsoidal (about 0.59 μm/1.18 μm for strain 21–23) in swollen sporangia and are located subterminally. All of the strains are found to be Gram positive.

The following physiological properties apply to the various strains of B. proteolyticus, as summarized in table 1:

TABLE 1

| Physiological properties | |
|---|---|
| VP test | Negative |
| Production of indole | Negative |
| Hydrolysis of starch | Positive |
| Utilization of citric acid | Slightly utilized in Koser's medium |
| Production of pigment | No extracellular pigment is formed |
| Catalase | Positive |
| Temperature range for growth | A temperature of 20–57° C., particularly 33 to 35° C. is good. |
| pH range for growth | pH 7.0 to 12.0 particularly, around pH 10.0 is good. |
| Behaviour to oxygen | Aerobic |
| Production of acids from saccharides given in table below : | |
| (+, produced; − not produced) | |

| Substrate | Strain 11–12 | Strain 11–13 | Straini 21–23 |
|---|---|---|---|
| erythritol | − | − | − |
| D-arabinose | − | − | − |
| L-arabinose | − | − | − |
| ribose | + | + | + |
| D-xylose | − | − | − |
| L-xylose | − | − | − |
| adonitol | − | − | − |
| 1-O-methyl β-D-xyloside | − | − | − |
| D-galactose | + | + | + |
| D-glucose | + | + | + |
| D-fructose | + | + | + |
| L-sorbose | − | − | − |
| L-rhamnose | − | − | − |
| dulcitol | − | − | − |
| inositol | − | − | − |
| D-mannitol | + | + | + |
| D-sorbitol | − | − | − |
| α-methyl D-mannoside | − | − | − |
| α-methyl D-glucoside | + | + | + |
| N-acetylglucosamine | + | + | + |
| amygdalin | + | + | + |
| esculin | − | − | − |
| salicin | + | + | − |
| D-cellobiose | + | + | + |
| D-maltose | + | + | + |
| lactose | − | − | − |
| melibiose | − | − | − |
| saccharose | + | + | + |
| trehalose | + | + | + |
| inulin | − | − | − |
| melezitose | − | − | − |
| raffinose | − | − | − |

TABLE 1-continued

| | | | |
|---|---|---|---|
| starch | + | + | + |
| glycogen | + | + | + |
| xylitol | − | − | − |
| β-gentiobiose | + | + | + |
| D-lyxose | − | − | − |
| D-fucose | − | − | − |
| D-arabitol | − | − | − |
| L-arabitol | − | − | − |
| gluconate | − | − | − |
| 2-keto gluconate | − | − | − |
| 5-keto gluconate | − | − | − |

Additional properties of these bacteria are their resistance to sodium chloride (all of the strains grow in 5% NaCl but not in 7% or 10% NaCl); their capability of production of alkaline proteases which have an optimal pH of 9 or higher and show excellent stability in alkaline conditions when combined with detergent constituents and therefore contribute to improved washing ability.

Summarizing the foregoing properties, the bacteria of the present invention are Gram-positive rods which are catalase positive, are aerobic and produce heat-resistant endospores. Thus, they belong to the genus Bacillus. The strains are also found to be rods having peritrichous flagella, to grow at a temperature range of 20° C. to 57° C. and to have an optimal growth temperature of 33° to 35° C. These strains are alkalophiles capable of growing at pH 10.

Known species of Bacillus having properties similar to the present strains are B. pasteurii and B. alcalophilus. The strains according to the invention differ from B. pasteurii in that the strains according to the invention hydrolyze starch while Bacillus pasteurii does not and the strains according to the invention do not require ammonium salts for propagation in an alkaline medium while B. pasteurii does. In addition the strains according to the invention do not grow in the presence of 10% NaCl while B. pasteurii does. Another distinction is that while the strains of B. proteolyticus described above are capable of growth at temperatures up to 55°–57° C., B pasteurii will not grow at 50° C. or above. Further, since the present strains are alkalophilic bacilli, they are compared to Bacillus alcalophilus (ATCC 27647). The present strains differ from the ATCC 27647 strain in that the strains according to the invention do not produce acid from L-arabinose or D-xylose while Bacillus alcalophilus does. Strain ATCC 27647 does not grow in the presence of 5% NaCl or at temperatures of 50° C. and above, conditions under which the present strains do grow. As only two Bacillus species capable of growth under alkaline conditions have been given names, the present strains are compared with the available unnamed alkalophilic Bacillus sp. No. 221 (ATCC 21522), No. Y-76 (ATCC 21537 - U.S. Pat. No. 4,052,262), No. 0–4 (ATCC 21536 - U.S. Pat. No. 4,052,262), N° A-40 (ATCC 21592), PB-92 (ATCC 31408 - U.S. Pat. No. 4,002,572) and strains Y, P, K and X (European Patent Application 0,204,342).

All of the strains mentioned above are alkalophilic bacteria and share the property of growth in alkaline medium (pH 10). In contrast to the present strains, Bacillus isolates Y, P, K and X will grow in the presence of 10% NaCl , will not grow above 47° C., do not produce acid from galactose and produce lemon shaped endospores. Bacillus strain PB-92 (ATCC 31408) in contrast to the present strains, produced acid only from ribose, no acid is formed from the other substrates tested (see Table 2), Bacillus strain PB-92 had a maximum temperature for growth of 50° C. A full comparison of the present strains from the species *B. proteolyticus* with Bacillus Nos. 0-4, A-40 and 221 in addition to all of the other ATCC strains mentioned is given in the following table 2:

TABLE 2

Characters Differentiating *Bacillus proteolyticus* From Other *Alkalophilic Bacilli*

| Acid Produced from | B. proteolyticus (all 3 strains) | B. alcalophilus ATCC-27647 | B. alcalophilus subsp. halodurans ATCC 27557 | No O-4 (ATCC-21536) | No Y-76 (ATCC-21537) | No 221 (ATCC-21527) | No A-40 (ATCC-21592) | PB-92 (ATCC-31408) |
|---|---|---|---|---|---|---|---|---|
| ribose | + | − | − | + | − | − | + | + |
| galactose | + | − | − | − | − | − | − | − |
| D-glucose | + | + | + | + | + | + | + | − |
| D-fructose | + | + | + | + | + | + | + | − |
| L-rhamnose | − | − | − | − | + | − | − | − |
| D-mannitol | + | − | − | − | + | + | + | − |
| D-sorbitol | − | − | − | − | + | + | − | − |
| α-methyl-D-glucoside | + | − | − | − | + | − | + | − |
| N-acetyl-glucosamine | + | + | + | + | + | + | + | − |
| amygdalin | + | − | − | + | + | + | − | − |
| esculin | − | + | − | − | − | − | + | − |
| O-cellobiose | + | − | − | + | + | + | − | − |
| D-maltose | + | + | + | − | + | + | + | − |
| saccharose | + | + | + | + | + | + | + | − |
| trehalose | + | + | + | + | + | + | + | − |
| starch | + | + | + | − | − | − | + | − |
| glycogen | + | + | + | − | − | − | + | − |
| β-gentiobiose | + | − | − | − | − | − | − | − |
| Maximum growth temp (°C.) | 55–57 | 46 | 54 | 56 | 56 | 55 | 47 | 47 |
| Growth in 5% NaCl | + | − | + | + | + | + | + | ND |
| Growth in 10% NaCl | − | − | + | ND | ND | ND | ND | ND | temp = temperature, ND = not determined, + = produced, − = not produced

Since the Bacilli strains of the present invention are clearly distinguishable from the known alkalophilic bacilli, *B. pasteurii*, *B. alcalophilus*, *B. alcalophilus* subsp. halodurans and the unnamed members of the alkalophilic bacilli, it is appropriate to establish a new species for the microorganism under consideration. Accordingly, we refer to this novel bacterial species as *Bacillus proteolyticus*.

The alkaline proteases of the present invention can be produced not only by the isolates of *Bacillus proteolyticus* herein described but also by natural or artificial mutants and/or other derivatives thereof.

The present invention concerns also a process for the production of the alkaline protease according to the invention which comprises cultivating the novel microorganisms or a derivate thereof in a suitable nutrient medium under aerobic conditions and then recovering the alkaline protease therefrom.

The alkaline proteases produced in accordance with the present invention may be prepared by cultivating a bacterial culture of *B. proteolyticus* or a derivative thereof and isolating and purifying the resultant as per known methods for producing alkaline proteases.

For cultivation of the present strains it is possible to use a solid or liquid culture medium, such culture medium must contain an alkaline buffer as well as components necessary for the bacteria's growth, i.e. a carbon source, a nitrogen source and inorganic salts.

The buffer should maintain the medium's pH at a level between 7 and 12 and preferably between 8 and 11.

Suitable carbon sources include glucose, mannose, fructose, mannitol, maltose, cellobiose, sucrose, dextrin, starch, hydrolyzed starch, molasses, their mixtures or a blend of two or more of these carbon sources. Preferably used carbon sources are glucose and/or hydrolyzed starch. The best results are obtained with hydrolyzed starch.

Nitrogen sources which can be used include soybean flour, hydrolyzed soybean flour, casein, corn steep liquor, cotton seed meal, potato flour, barley flour, enzymatic hydrolyzates of available proteins, non-fat dry milk solids, dried yeast, yeast extract, their mixtures or a blend of two or more of these nitrogen sources. Preferably used nitrogen sources are soybean flour, hydrolyzed soybean flour, cotton seed meal, enzymatic hydrolyzates of proteins, non-fat dry milk solids, yeast extract and a blend of two or more of these compounds. More preferably nitrogen sources are soybean flour, hydrolyzed soybean flour, cotton seed meal, yeast extract and a blend of two or three of these compounds. The best results are obtained with hydrolyzed soybean flour.

Potassium phosphate, calcium chloride, calcium chloride dihydrate, sodium sulfate, sodium citrate dihydrate, magnesium sulfate and their mixtures represent suitable inorganic salts.

Examples of suitable alkaline buffers include disodium hydrogen phosphate, dipotassium hydrogen phosphate, sodium carbonate, potassium carbonate, sodium bicarbonate, sodium phosphate, sodium tetraborate and a blend of two or more of these buffers. Preferably used alkaline buffers are disodium hydrogen phosphate, dipotassium hydrogen phosphate, sodium carbonate, sodium bicarbonate, sodium phosphate or a blend of two or more of these buffers.

Alternatively an automatic pH control scheme may be employed by the addition of various basic reacting substances. If desired there can be added other organic or inorganic substances necessary for the growth of the bacterial strains or the production of enzymes.

The media containing the above components are sterilized in a conventional manner and inoculated with one of the strains of the present invention. Cultivation may be conducted aerobically with shaking or under aerated agitation preferably at 30° to 40° C. for 30 to 120 hours to obtain a culture fluid.

After removal of biomass by known methods, such as microfiltration, centrifugation, ultrafiltration, flocculation and/or flocculation followed by ultrafiltration or centrifugation, the supernatant is subjected to one or more processes such as conventional salting out, precipitation by the addition of an organic solvent, ultrafiltration, condensation under reduced pressure, ion-exchange or gel filtration to collect crude or purified enzymes in the form of a powder or concentrated liquid. All of the strains described herein produce a pattern of three alkaline proteases with isoelectric points ranging from 10 to 11.5 (as determined by chromatofocusing).

The major protease enzyme can be purified as follows: After cultivation of the bacterium the culture fluid is centrifuged to obtain a supernatant. To this supernatant, a flocculating agent such as the product sold under the trademark CYNCAL, water and an aid in filtering such as a compound containing dicalcium silicate and dicalcium aluminate or the compound sold under the trademark CELITE are added and thoroughly mixed.

The resulting slurry is filtered. The proteases are precipitated from the resulting clear filtrate by traditional salting out wherein solid sodium sulphate is added and stirred. A compound containing dicalcium silicate and dicalcium aluminate is then added and filtered using a precoated filter. The retained solids are then dried under reduced pressure. The dry powder is then extracted with a buffer. Undissolved material is removed by slow speed centrifugation and the resulting supernatant clarified by filtration. The solution is then diafiltered against water using an ultrafilter to remove salts. The resulting solution is then applied to an ion-exchange column, such as a DEAE-cellulose (Whatman) ion-exchange column, that is previously equilibrated with a buffer, such as with 0.01 M sodium phosphate buffer (pH 6.5) and eluted with the same buffer. The protease is not bound by the support and eluted at the void volume. This is then applied to a column containing agarose to which a blue dye affinity ligand is bound. The protease is bound on the agarose column and is eluted. The eluate from the latter column is diafiltered to remove salts and the retentate is lyophilized resulting in a purified protease preparation.

The present invention concerns also detergent compositions containing at least the alkaline protease according to the invention.

The present invention concerns also washing compositions containing an effective amount of the alkaline protease according to the invention.

The enzyme may be formulated into washing compositions in the usual manner and washing compositions containing the enzyme form another aspect of the invention. The washing compositions containing the enzyme of the invention further contain at least a detergent. Detergents useful in the washing compositions and compatible with enzyme addition are generally non-ionic and anionic surface-active compounds, such as water-soluble soaps, anionic, non-ionic, ampholytic and zwitterionic detergents.

An example of a commonly used detergent is sodium dodecylbenzene sulfonate, alternatively sodium linear alkyl benzene sulfonate and primary alkyl sulfate. Preferably it is sodium dodecylbenzene sulfonate.

An example of nonionic detergent is ethoxylate of an approx. $C_{13}$-$C_{15}$ primary alcohol with 7 ethoxylate residues per mole or a mixture of this with the corresponding alcohol ethoxylated to the extend of 3 residues per mole.

The above washing compositions may contain additional compounds which are commonly used in detergent formulations containing proteolytic activity. They can contain complex phosphates such as an alkali metal tripolyphosphate, such as sodium tripolyphosphate or an alkali metal pyrophosphate. Furthermore, or alternatively, compounds such as alkali metal cyanotriacetate and alkali metal citrate may be included. Their action in washing compositions is complex, but their most important action is that of water softeners.

Other compounds which are usually incorporated are a structurant, for example, an alkali metal silicate, and preferably sodium silicate, weakly alkaline compounds, such as an alkali metal bicarbonate, fillers such as an alkali metal sulfate, and preferably sodium sulfate, and other compounds such as carboxymethyl cellulose, sodium carboxymethyl cellulose, perfumes and optical brighteners.

Another usually incorporated compound is a perborate bleach precursor such as an alkali metal perborate, and preferably sodium perborate.

In formulation, preferably the enzyme is mixed with one of the components, such as the filler, to make a concentrate of known enzymatic activity, which then can be mixed with the other desired components.

The washing compositions may also contain an alkali to adjust to desired pH and neutral inorganic salt, such as sodium sulfate.

The washing compositions may also contain acrylic polymer, such as polyacrylic acid, alternatively acrylic/maleic copolymer.

The washing compositions may also contain amino-containing bleach activator, such as tetra-acetyl-ethylene-diamine.

The washing compositions may also contain zeolite as builder, such as type A ZEOLITE.

The washing composition according to the invention may contain other enzymes than the alkaline protease as defined here above. It may contain neutral protease, alkaline protease, protease derived from *Bacillus subtilis, Bacillus lentus, Bacillus amyloliquefaciens, Bacillus licheniformis* or *B. alcalophilus*, amylase, cellulase, lipase or a blend of two or more of these other enzymes.

An example of washing composition may contain the enzyme according to the invention and a detergent, a water softener, an alkali metal silicate, a weakly alkaline bicarbonate and optionally an alkali metal borate.

An example of an aqueous detergent liquid according to the invention is formulated to contain dodecylbenzene sulfonic acid, $C_{12}$-$C_{15}$ linear alcohol condensed with 7 mol/mol ethylene oxide, monoethanolamine, citric acid, sodium xylenesulfonate, sodium hydroxide, protease according to the invention and water.

The present invention concerns also a detergent composition containing a detergent-active composition and an effective amount of the alkaline protease as defined here above.

The present invention concerns also a granular detergent composition containing a detergent-active composition and an effective amount of the alkaline protease as defined here above and also comprising at least one of a builder, bleach or whitening agent.

Many such builder, bleach or whitening agents are known in the art.

The present invention concerns also a liquid detergent composition containing a detergent-active composition and an effective amount of the alkaline protease as defined here above and also comprising at least one of a bleach or whitening agent.

The present invention concerns also a liquid detergent composition comprising the alkaline protease as defined here above. This liquid detergent composition can be aqueous or nonaqueous. Often this liquid detergent composition contains an enzyme stabilizer to improve the storage stability. Many such enzyme stabilizers are known in the art, e.g. a polyol such as propylene glycol. The invention particularly relates to a homogeneous concentrated liquid detergent.

The present invention concerns also a granular detergent composition comprising the alkaline protease as defined here above.

The present invention concerns also a method for removing protein stains from cloth, said method comprising washing said cloth with a detergent composition as defined here above.

The present invention is further illustrated by the following examples.

EXAMPLE 1

The screening procedure used to isolate the strains of the invention from the natural field is carried out as follows:

1) Isolation of alkalophilic bacteria:

About 1 g of soil from the sample sites under investigation is suspended in 9 ml of a saline solution (0.8% NaCl). A volume of this suspension (0.1–1.0 ml) is spread on the surface of an agar plate containing the following medium: 0.8% (w/v) hydrolyzed soybean flour sold under the trademark HY SOY (Sheffield Products), 0.044% (w/v) calcium chloride, 2.1% (w/v) hydrolyzed starch sold under the trademark MALTRIN 100 (Grain Processing), 2% (w/v) non-fat dry milk solids, 0.84% (w/v) sodium bicarbonate and 0.1% disodium hydrogen phosphate. This is solidified with 1.5% agar. Incubation of the plates is carried out at 32° C. for 3 days to obtain alkalophilic bacilli.

2) Isolation of alkaline protease - producing bacteria

The alkalophilic bacteria obtained in the procedure (1) above are further purified on plates of the same medium and incubated at 32° C. for 2 days, then ones which formed clearing halos are collected as alkaline protease-producing bacteria.

3) High temperature screen

All of the bacteria selected in the procedure (2) above are restreaked on the same medium and examined for growth at 57° C. after 48 hours incubation.

4) Selection of stable alkaline protease producers

All of the bacteria selected in the procedure (3) above are grown in a liquid medium comprising 0.5% hydrolysate of proteins sold under the trademark TRYPTONE (Difco Labs), 0.5% yeast extract, 1.0% glucose, 0.42% sodium bicarbonate, 0.53% sodium carbonate, 0.1% dipotassium hydrogen phosphate. These are incubated at 37° C. with shaking at 200 rpm overnight. This is then transferred to a second batch of the same medium at a 5% (v/v) inoculum level and incubated with shaking at 37° C. for 5% hours. A 5% inoculum is then transferred to a protease production medium comprising 2.4% soy flour, 4.8% hydrolyzed starch sold under the trademark MALTRIN 100 (Grain Processing), 0.9% disodium hydrogen phosphate and 1.0% sodium bicarbonate pH 9.5 and incubated at 37° C. for 40 hours with vigorous agitation (300 rpm). The biomass is removed by low speed centrifugation and protease stability at pH 9.5 at 55° C. is examined in the following manner. 50 µl of alkaline protease containing supernatant is applied to 12.7 mm blank paper antibacterial test discs on the surface of agar plates of the composition described in the procedure (1) above. The size of the clearing zones of protease activity is monitored over a 10-hour period, while being incubated at 55° C. A continued expansion in zone size is taken to signify enhanced stability.

All of the bacteria selected are examined, characterized and classified according to R. E. Gordon (1973) and Bergey's Manual of Systematic Bacteriology, Vol. 2 (1986). In addition the production of acid from carbohydrates is examined using a modification of the miniaturized test system API rapid CH (DMS Laboratories, Inc., N.J.). In this protocol, the organisms are applied to alkaline nutrient agar plates made by addition of 1.0% sodium bicarbonate and 0.9% disodium hydrogen phosphate to NUTRIENT AGAR (Difco) and incubated at 35° C. for 48–72 hours. Growth of 5 plates per organism is resuspended in 25 ml of Thymol blue solution (comprising 0.5% TRYPTONE (Difco), 0.5% yeast extract, 0.5% sodium sulfate and 0.015% thymol blue (Fisher Scientific Co. N.J.) adjusted to pH 9.2 with 10N NaOH. This is then added into the ampoules of the microassay kit and any change of color from the blue starting point is recorded over a 48-hour period. The most stable-alkaline protease producers all produce a characteristic pattern of acid production on the carbohydrates, that is unlike that obtained from any other alkalophilic Bacillus and thus warrants creation of a new species of Bacillus: *Bacillus proteolyticus*. This cluster of bacteria, isolated from natural sources includes *B. proteolyticus* strains 11–12, 11–13 and 21–23. These bacteria *Bacillus proteolyticus* are deposited with the Agricultural Research Culture Collection (Peoria, Ill., USA) under the Budapest Treaty. The deposit numbers are as follows: *Bacillus proteolyticus* strain 11–12: NRRL B-18964, *Bacillus proteolyticus* strain 11–13: NRRL B-18963, *Bacillus proteolyticus* strain 21–23: NRRL B-18965.

EXAMPLE 2

Culture of Strains

A frozen working culture (stored in 10% glycerol) of *Bacillus proteolyticus* strain 21–23 (NRRL B-18965) is used to inoculate a seed medium which contained 0.5% TRYPTONE (Difco) 0.5% yeast extract (Difco) and 1.0% glucose in deionized water. It also contained 0.9% disodium hydrogen phosphate and 1.0% sodium bicarbonate. This buffer solution is prepared as a concentrate, adjusted to pH 9.5 with NaOH, sterilized separately and added to the seed flask when cool. The culture is incubated with shaking at 34° C. until the culture reaches a cell density equivalent to a Klett value of 400 units as measured on a Klett-Sommerson photometer (Klett Manufacturing Co., N.Y., USA). This culture is used to inoculate (with a 5% inoculum level) ten liters of the same medium in a ten-liter fermentor, which is then cultivated with aeration (0.5 vvm) and stirring (500 rpm) at 34° C. until the culture again reaches a cell density equivalent to 400 Klett units. From this a 100-liter production fermentor is inoculated with a 5% inoculum level. This fermentor contains 0.33% sodium citrate dihydrate, 0.26% calcium chloride dihydrate, 1.87% hydrolyzed soybean flour sold under the trademark HY SOY (Sheffield), 2.93% cotton seed meal sold under the trademark PHARMAMEDIA (Traders Protein), 10.93% hydrolyzed starch sold under the trademark MALTRIN M-50 (Grain Processing), 0.2% defoamer sold under the trademark MAZUR P-2000 defoamer (Mazur Chemical Co.) with softened water. The buffer contains 0.9% disodium hydrogen phosphate and 1.0% sodium bicarbonate in deionized water (7.0% of final volume). It is adjusted to pH 9.7 with NaOH and sterilized separately. The final pH of the complete medium is adjusted to 9.7 with NaOH. This is then cultivated at 34° C. for 78 hours with aeration (0.5 vvm) and stirring (400 rpm) under 10 psi back pressure. After 78 hours of cultivation, the yield of alkaline protease is 37 APU/ml supernatant.

EXAMPLE 3

Purification of the Alkaline Protease

The major protease enzyme is purified from *B. proteolyticus* strain 21-23 (NRRL B-18965) as follows. After cultivation of the bacterium the culture fluid is centrifuged at 1,300 rpm (27,300 g) for 60 minutes to obtain a supernatant. To 4 l of supernatant, 50 g of a flocculating agent sold under the trademark CYNCAL (50% w/w), 150 ml water and 200 g of a compound containing dicalcium silicate and dicalcium aluminate sold under the trademark CELITE 512 are added and thoroughly mixed. The resulting slurry is filtered using a filter precoated with the product sold under the trademark CELITE 512. The proteases are precipitated from the resulting clear filtrate by traditional salting out wherein solid sodium sulphate is added to give a final concentration of 29% (w/v) and stirred for 1 hour. Approximately 50 g of the product sold under the trademark CELITE 512 is then added and filtered using a CELITE 512 precoat filter. The retained solids are then dried under reduced pressure at 0° C. for 48 hours. The dry powder is then extracted with 0.1 M sodium phosphate buffer (pH 6.5). Undissolved material is removed by slow speed centrifugation and the resulting supernatant clarified by filtration through a 0.45 micron filter. The solution is then diafiltered against water using a 10,000 molecular weight cut-off ultrafilter membrane to remove salts. The resulting solution is then applied to a DEAE-cellulose (Whatman) ion-exchange column that is previously equilibrated with 0.01 M sodium phosphate buffer (pH 6.5) and eluted with the same buffer. The protease is not bound by the support and is eluted at the void volume. This is then applied to a column containing agarose to which a blue dye affinity ligand is bound. The ligand is available commercially from Pierce Chemicals as CIBACRON BLUE F3GA. The protease is bound on the CIBACRON BLUE agarose column and is eluted with a solution of 0.5 M NaCl in 0.01 M sodium phosphate buffer (pH 6.5). The eluate from the latter column is diafiltered as previously described to remove salts and the retentate is lyophilized resulting in a purified protease preparation.

EXAMPLE 4

Properties of the Alkaline Protease

The physicochemical properties of the major novel alkaline protease produced by the *B. proteolyticus* strain 21-23 so obtained are as follows:

i) Specific Activity

The specific activity of the purified novel alkaline protease from strain 21-23 is calculated to be 26.5 APU/mg protein.

Analytical protocols: The alkaline protease assay is based on the hydrolysis at 40° C. of a casein substrate (at a concentration of 0.67% w/v buffered at pH 8.5 with 0.06 M borate buffer (pH 8.5). Unhydrolyzed substrate is precipitated by addition of 18% (w/v) trichloroacetic acid and removed by centrifugation (1800 g for 15 minutes). Solubilized casein peptides are measured by absorbance at 275 nm. One alkaline protease unit (APU) is that activity which will liberate the equivalent of four micromoles of tyrosine per minute under the conditions of the assay. Protein concentration is determined by using the BRADFORD protein reagent (obtained from Sigma Chemical Co., St. Louis, Mo.) under the conditions recommended by the manufacturer.

ii) Isoelectric Point

The isoelectric point of the alkaline protease is 11.1 as estimated by chromatofocusing. This is also confirmed by isoelectric focusing using the PHARMACIA ampholyte system (Pharmacia Inc., Piscataway, N.J.).

iii) Molecular Weight

The molecular weight of the purified alkaline protease is determined by polyacrylamide gel electrophoresis in the presence of sodium dodecylsulphate. The molecular weight is found to be 28 Kdaltons.

iv) Amino Acid Sequence Analysis

The lyophilized purified alkaline protease is partially sequenced from the amino terminus using an APPLIED BIOSYSTEMS (Foster City, Calif.) 477A Pulsed Liquid Phase Protein Sequencer, operated according to the manufacturers instructions. The sequence of the first 20 amino acids from the amino terminal are given below in the standard 3 letter amino acid code.

Ala-Gln-Ser-Val-Pro-Trp-Gly-Ile-Ser-Arg-Val-Gln-Ala-Pro-Ala-Ala-His-Asn-Arg-Gly v) Stability in Detergent Formulations A commercial heavy duty liquid detergent is titrated to either pH 8 or pH 9.6 and either a sample of the new protease is added or a sample of the alkaline protease produced by *B. licheniformis* (Enzyme A) is added for comparison, both proteases are added to approximately 2.0 APU/g detergent. The samples are then incubated at 43° C. and assayed for activity on the days indicated and the remaining activity measured. The values are expressed in relative activity on the basis of the activity at the time of 0 day (at 100). The first number in the following table 3 refers to the remaining activity with a pH 8.0 treatment and the number in parentheses refers to the remaining activity when held at pH 9.6.

TABLE 3

| Enzyme Source | Remaining Activity at Day | | | |
|---|---|---|---|---|
| | 0 | 4 | 7 | 11 |
| New Protease *B. proteolyticus* | 100(100) | 80(71) | 68(54) | 74(55) |
| Enzyme A *B. licheniformis* | 100(100) | 34(25) | 24(18) | 21(15) | vi) Optimal pH Range for Activity

The relative activities of the new protease in comparison to Enzyme A from *B. licheniformis* are determined using a variety of buffer solutions in the pH range of 6.5 to 11.5. The activity obtained at pH 8.5 is arbitrarily assigned as 100. The data are given in the following table 4. This table 4 shows that the novel protease from *B. proteolyticus* has greater activity above pH 8.5 than the protease from *B. licheniformis* and this difference is most dramatic under highly alkaline conditions.

TABLE 4

| Enzyme Source | Remaining Activity at pH | | | | | |
|---|---|---|---|---|---|---|
|  | 6.5 | 7.5 | 8.5 | 9.5 | 10.5 | 11.5 |
| New Protease *B. proteolyticus* | 50 | 82 | 100 | 107 | 105 | 110 |
| Enzyme A *B. licheniformis* | 66 | 89 | 100 | 97 | 97 | 64 |

The properties of the alkaline protease produced by *B. proteolyticus* strain 21-23 is compared with other known alkaline proteases, and as can be seen in the Table 5, the protease from strain 21-23 has a unique molecular weight and isoelectric point and hence is recognized as a novel alkaline protease.

TABLE 5

| Organ. Ref. | 21-23 | *Bacillus sp. Y* a | | *B. licheniformis* b Carlsberg | *B. sp.*221 | NKS-21 d |
|---|---|---|---|---|---|---|
| Enzyme | New protease | 1/a | 1/b | subtilisin | c | API-21 |
| Molec. weight | 28,000 | 21,000 | 40,000 | 27,300 | 30,000 | 22,000 |
| Isoel. point | 11.1 | 10.1 | 5.1 | 9.4 | 10.0 | 7.4 | a : European patent application 0,204,342
1/a : alkaline protease Ya derived from *Bacillus sp.*Y
1/b : alkaline protease Yb derived from *Bacillus sp.*Y
b : Markland, Jr. F.S. & Smith, E.L. (1971), Subtilisins : primary structure, chemical and physical properties. The Enzymes (3 ed.), Vol. 3 pp. 561–608, Academic Press, New York and London.
c : U.S. Pat. No. 4,052,262
d : U.S. Pat. No. 4,480,037
Ref. = reference
Organ. = Organism
Molec. weight = Molecular weight
Isoel. point = Isoelectric point

EXAMPLE 5

Use of Novel Alkaline Proteases in Detergents

Washing tests are carried out in the following manner with test pieces of cloth: EMPA-117 or EMPA-116 stained with blood, milk and chinese ink or EMPA-112 stained with Cocoa, milk and sugar (obtained from Eidgenossiche Material Prufungs und Versuchanstalt fur Industrie, Bauwesen und Gewerbe at Skt Gallen, Switzerland) using a commercial, high carbonate anionic detergent with an initial pH in the wash water of 10.7. Alkaline protease, obtained in example 3, is added at a use level of 20 APU/l. A Terg-o-tometer (US-Testing Co.) is used as a washing machine. Four cloths are added to 1.0 liter of wash water and washed at 100 rpm, 38° C. for 10 minutes. Rinsing is carried out with 10 liters of water for 5 minutes. The percent soil removal is calculated using the following formula.

$$\% \text{ soil removal} = (RW - RS)/(RO - RS) \times 100$$

where RO = Reflectance of unstained cloth
RS = Reflectance of stained cloth
RW = Reflectance of washed cloth
The results are shown in the Table 6.

TABLE 6

| Sample | Source | % soil removal, Stained cloth | | |
|---|---|---|---|---|
|  |  | EMPA 116 | EMPA 117 | EMPA 112 |
| Detergent alone | — | 4 | 19 | 4 |
| Enzyme A | *B. licheniformis* | 22 | 56 | 17 |
| New Protease | *B. proteolyticus* | 28 | 60 | 22 |

Enzyme A = Carlsberg subtilisin from *B. licheniformis* described in table 5 (under ref. b).

The table 6 shows that under the test conditions the enzyme of the invention has a better washing action than a commercially available enzyme derived from *B. licheniformis*.

---

We claim:

1. A purified alkaline protease from a bacterium of the species *Bacillus proteolyticus* NRRL B-18964, *Bacillus proteolyticus* NRRL B-18963 or *Bacillus proteolyticus* NRRL B-18965 having:

an amino acid terminal sequence corresponding to Seq. ID No.: 1 as follows:

Ala-Gln-Ser-Val-Pro-Trp-Gly-Ile-Ser-Arg-Val-Gln-Ala-Pro-Ala-Ala-His-Asn-Arq-Gly-;

a molecular weight of 28 Kdaltons and an isoelectric point from 10 to 11.5;

an optimal pH for proteolytic activity at a pH in the range of 8.5 through 11.5;

said alkaline protease retaining at least 70% of its original activity after being held at a pH of 8.0 at a temperature of 43° C. for a period of 11 days.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 20 amino acids
        ( B ) TYPE: Amino Acid
        ( D ) TOPOLOGY: Linear ( i i ) MOLECULE TYPE: Protein ( v ) FRAGMENT TYPE: N-Terminal Fragment ( i x ) FEATURE:
        ( A ) NAME/KEY: Amino Terminal Sequence (B) LOCATION: +1 to +20

(x) PUBLICATION INFORMATION:
    (A) AUTHORS: Vetter, Roman
                    Wilke, Detlef
                    Amory, Antoine
                    Clippe, Andr
                    Aehle, Wolfgang
                    Schomburg, Dietmar
    (B) TITLE:
    (C) JOURNAL:
    (D) VOLUME:
    (E) ISSUE:
    (F) PAGES: 25, FIG. 1
    (G) DATE:
    (H) DOCUMENT NUMBER: EP-A 0 415 296
    (I) FILING DATE: August 25, 1990
    (J) PUBLICATION DATE: March 6, 1991
    (K) RELEVANT RESIDUES IN SEQ ID NO: 1: From 1 to 20

(xi) SEQUENCE DESCRIPTION: SEQ IS NO:1:

```
Ala  Gln  Ser  Val  Pro  Trp  Gly  Ile  Ser  Arg
 1              5                        10
Val  Gln  Ala  Pro  Ala  Ala  His  Asn  Arg  Gly
15                   20
```